United States Patent
Huang et al.

(10) Patent No.: US 12,385,916 B2
(45) Date of Patent: Aug. 12, 2025

(54) SERUM METABOLIC BIOMARKERS AND KIT FOR DETECTING DRUG-RESISTANT TUBERCULOSIS

(71) Applicant: Zhejiang SUKEAN Pharmaceutical Co., Ltd., Hangzhou (CN)

(72) Inventors: Pintong Huang, Hangzhou (CN); Yajing Liu, Hangzhou (CN); Yan Su, Hangzhou (CN); Chao Zhang, Hangzhou (CN)

(73) Assignee: Zhejiang SUKEAN Pharmaceutical Co., Ltd., Hangzhou (CN)

( * ) Notice: Subject to any disclaimer, the term of this patent is extended or adjusted under 35 U.S.C. 154(b) by 0 days.

(21) Appl. No.: 18/350,761

(22) Filed: Jul. 12, 2023

(65) Prior Publication Data
US 2023/0349900 A1  Nov. 2, 2023

Related U.S. Application Data

(63) Continuation of application No. PCT/CN2022/136422, filed on Dec. 5, 2022.

(51) Int. Cl.
*G01N 33/00* (2006.01)
*G01N 33/569* (2006.01)

(52) U.S. Cl.
CPC ..... *G01N 33/5695* (2013.01); *G01N 2333/35* (2013.01); *G01N 2570/00* (2013.01)

(58) Field of Classification Search
CPC ........... G01N 33/5695; G01N 2333/35; G01N 2570/00; G01N 27/64; G16B 5/20; G16B 50/00; G16H 50/20

USPC .......................................................... 436/16
See application file for complete search history.

(56) References Cited

U.S. PATENT DOCUMENTS

| | | | |
|---|---|---|---|
| 2009/0104602 A1* | 4/2009 | Fernandez-Reyes | G01N 33/5695 435/6.15 |
| 2014/0256664 A1* | 9/2014 | Houpt | A61K 31/4409 514/354 |

* cited by examiner

*Primary Examiner* — Elizabeth A Robinson
*Assistant Examiner* — Emily R. Berkeley
(74) *Attorney, Agent, or Firm* — Andrew C. Cheng

(57) ABSTRACT

A set of serum metabolic biomarkers and detection kit for detecting drug-resistant tuberculosis are provided. The set of the serum metabolic biomarkers includes 17 serum metabolic biomarkers. The 17 serum metabolic biomarkers are verified to be associated with tuberculosis based on the level changes of these biomarkers. The 17 metabolites includes taurine, homocysteine, uric acid, ascorbic acid, suberylglycine, uridine, dopamine 4-sulfate, inosinic acid, glyceraldehyde phosphate, [3-methoxy-4-(phosphoryl)phenyl]carbonyl sulfonic acid, nuclomedone, n4-cyclopropyl-6-(2,3-dichlorophenyl)-1,2,3,4-tetrahydropyrimidine-2,4-diimine, 1-[2-chlorine-2-(2,4-dichlorophenyl)ethenyl]-1,2,4-triazole, tetrachloro-phthalic anhydride, malotilate, fulvic acid, and L-neopterin. The serum metabolic biomarkers and detection kit for detecting drug-resistant tuberculosis can assist doctors in accurately diagnosing the disease, which is of great significance for the diagnosis and mass screening for drug-resistant tuberculosis.

1 Claim, 1 Drawing Sheet

SERUM METABOLIC BIOMARKERS AND KIT FOR DETECTING DRUG-RESISTANT TUBERCULOSIS

CROSS REFERENCE TO RELATED APPLICATION

This application is a Continuation of PCT Patent Application No. PCT/CN2022/136422 filed on Dec. 5, 2022, which claims priority of China Patent Application No. 202210321968.9, filed on Mar. 29, 2022. The contents of the above-identified applications are incorporated herein by reference.

TECHNICAL FIELD

The disclosure relates to biology technologies, in particular to serum metabolic biomarkers and a kit for detecting drug-resistant tuberculosis.

BACKGROUND

A total of 1.6 million people died from tuberculosis (TB) in 2021. Globally, tuberculosis is the second largest infectious cause of death following COVID-19. The treatment of tuberculosis involves long-term administration of multiple drugs, but *Mycobacterium tuberculosis* (MTB) has the potential to develop resistance to one or more of these drugs, leading to treatment challenges. Drug-resistant tuberculosis (DR-TB) poses an increasing global threat to public health and safety. There is a pressing need to make concerted efforts to enhance the detection and diagnosis of drug-resistant tuberculosis. According to the guidelines provided by the World Health Organization (WHO), the detection of drug-resistant tuberculosis requires confirming the presence of tuberculosis through bacteriological methods, followed by the identification of drug resistance using rapid molecular tests or culture techniques. The diagnosis of drug-resistant tuberculosis is complex, costly, and requires a high level of technical expertise and adherence to laboratory biosafety measures. Consequently, it is limited in economically underdeveloped regions, impeding early tuberculosis control efforts. The diagnosis of drug-resistant tuberculosis are urgently required, and the identification of biomarkers for drug-resistant tuberculosis holds great significance.

Therefore, there is a critical need to improve the detection and diagnosis of drug-resistant tuberculosis.

SUMMARY

The disclosure presents, in its first aspect, a set of serum metabolic biomarkers for the detection of drug-resistant tuberculosis. These biomarkers consist of 17 specific metabolites found in the serum of patients with tuberculosis. The identified metabolites include taurine, homocysteine, uric acid, ascorbic acid, suberylglycine, uridine, dopamine 4-sulfate, inosinic acid, glyceraldehyde phosphate, [3-methoxy-4-(phosphoryl)phenyl] carbonyl sulfonic acid, nuclomedone, n4-cyclopropyl-6-(2,3-dichlorophenyl)-1,2,3,4-tetrahydropyrimidine-2,4-diimine, 1-[2-chlorine-2-(2,4-dichlorophenyl)ethenyl]-1,2,4-triazole, tetrachlorophthalic anhydride, malotilate, fulvic acid, and L-neopterin.

These metabolic biomarkers, described in the disclosure, demonstrate high sensitivity and specificity for detecting both drug-resistant tuberculosis and sensitive tuberculosis cases, making them crucial for effective tuberculosis treatment.

In the second aspect of the disclosure, a detection kit for drug-resistant tuberculosis is provided. This kit comprises specific detection reagents designed for the quantitative measurement of the aforementioned 17 metabolites present in the serum of tuberculosis patients. The 17 metabolites, as mentioned earlier, encompass taurine, homocysteine, uric acid, ascorbic acid, suberylglycine, uridine, dopamine 4-sulfate, inosinic acid, glyceraldehyde phosphate, [3-methoxy-4-(phosphoryl)phenyl] carbonyl sulfonic acid, nuclomedone, n4-cyclopropyl-6-(2,3-dichlorophenyl)-1,2,3,4-tetrahydropyrimidine-2,4-diimine, 1-[2-chlorine-2-(2,4-dichlorophenyl)ethenyl]-1,2,4-triazole, tetrachlorophthalic anhydride, malotilate, fulvic acid, and L-neopterin.

The present disclosure also provides a screening method for detecting tuberculosis by analyzing serum metabolic biomarkers. The screening method consists of the following steps: 1. Collection of 1-2 mL of blood from both tuberculosis (TB) patients and healthy individuals who are in a fasting state, using a venous blood collection tube (BD, 367955 SST II). 2. Centrifugation of the collected blood at 4° C. and 3500 rpm for 10 minutes, within two hours of collection. 3. Separation of the upper serum (0.3 mL to 1.5 mL) from the centrifuged blood into a new EP tube, followed by storage at −80° C. 4. Preparation for the LDI MS experiment, which involves dispersing iron particles in water at a concentration of 1 mg/mL as a substrate, diluting the upper serum 10 times with water, placing 1 μL of the diluted serum on a polishing plate, and adding 1 μL of the substrate to the diluted serum. 5. Analysis of each serum sample using the LDI MS technique, and recording the original metabolic fingerprints on an AutoFlex TOF/TOF mass spectrometer (Bruker, Germany). 6. Pre-processing of the original metabolic fingerprints using MATLAB (R2016a, the MathWorks, USA) to make them suitable for statistical analysis. This pre-processing includes baseline correction, peak detection, extraction, comparison, normalization, and standardization. 7. Training the data by randomly selecting ¾ of the data as the training set and using ¼ as the testing set. This is done using the Partial Least Squares (PLS) algorithm. 8. Establishment of a detection model and creation of a receiver operating characteristic (ROC) curve for the data using the Random Forest (RF) algorithm. 9. Performance of variance analysis and enrichment analysis of the data using MetaboAnalyst 5.0 software. 10. Selection of differential data based on the detection model. The selected data must meet the following criteria: a frequency greater than 90%, a p-value less than 0.05, and a VIP value greater than 1. These selected differential data are then compared with spectrogram information in the human Metabolome database (HMDB) to identify the metabolites that serve as the 17 serum metabolic biomarkers for tuberculosis detection.

A drug-resistant tuberculosis detection model utilizing the Random Forest (RF) algorithm in machine learning is established based on 17 carefully selected serum metabolic biomarkers. The aforementioned steps are followed to process the blood samples of patients undergoing testing in order to obtain the necessary data. Subsequently, the data is input into the drug-resistant tuberculosis detection model to identify the presence of drug-resistant tuberculosis in the tuberculosis patients. Another aspect of this disclosure pertains to a drug-resistant tuberculosis detection kit that includes diagnostic reagents for the 17 serum metabolic biomarkers specific to tuberculosis patients. This detection kit enables the quantitative assessment of the aforementioned biomarkers in the serum of tuberculosis patients.

For the first time, the disclosure has discovered an association between the aforementioned 17 metabolic biomarkers and pulmonary tuberculosis. Through metabolomics analysis, it is observed that the levels of these 17 metabolites in the serum of tuberculosis patients deviate from the norm. By integrating these 17 serum metabolic biomarkers with metabolomics analysis and machine learning, a highly effective drug-resistant tuberculosis detection model is established, which is subsequently evaluated using the ROC curve. The drug-resistant tuberculosis detection model, based on the levels of these 17 metabolic biomarkers, exhibits an outstanding performance with an area under the ROC curve of 98% for drug-resistant and sensitive tuberculosis detection, demonstrating a sensitivity of 90% and a specificity of 96%.

This disclosure harnesses the potential of serum metabolomics technology and machine learning methods to identify suitable biomarkers and construct a detection model for drug-resistant tuberculosis. The developed drug-resistant tuberculosis detection model offers exceptional effectiveness, characterized by high sensitivity and commendable specificity, rendering it suitable for detecting drug-resistant tuberculosis. Furthermore, this disclosure enables drug-resistant tuberculosis diagnosis through a straightforward blood test, which is not only rapid but also requires a small sample size of only 50 nL, thus facilitating mass screening for drug-resistant tuberculosis and holding significant clinical value.

BRIEF DESCRIPTION OF THE DRAWINGS

In order to illustrate the technical solution in the embodiments of the disclosure or the prior art more clearly, a brief description of drawings required in the embodiments or the prior art is given below. Obviously, the drawings described below are only some of the embodiments of the disclosure. For ordinary technicians in this field, other drawings can be obtained according to the structures shown in these drawings without any creative effort.

DETAILED DESCRIPTION OF THE EMBODIMENTS

Figure 1:
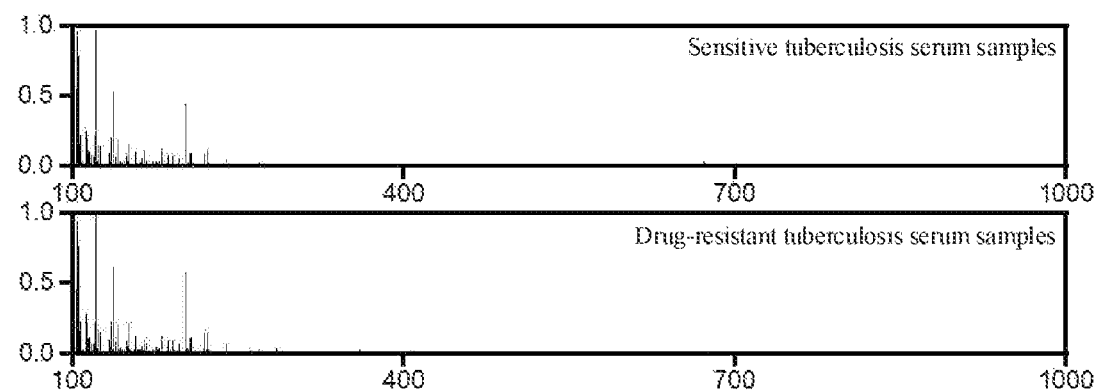
FIG. 1 illustrates a typical spectrum from a healthy control and a tuberculosis patient

To provide a clearer understanding of the purpose, technical solution, and advantages of the disclosure, it is further elaborated in conjunction with the drawings and embodiments. It should be noted that the specific embodiments described herein are intended solely for explanatory purposes and should not be construed as restrictive definitions. Any other embodiments that are obtained by those skilled in the field without involving any creative effort are also protected by the disclosure.

The use of terms such as "first," "second," "third," "fourth," if any, in the specification, claims, and drawings of this application is solely for the purpose of distinguishing similar objects and does not necessarily denote a specific order or sequence of priorities. It should be understood that the interchangeable use of these terms is appropriate, meaning that the described embodiments can be implemented in a different order or arrangement than what is explicitly illustrated or described. Furthermore, the terms "include" and "have," along with any variations, may encompass additional elements or components. For example, processes, methods, systems, products, or equipment described as comprising a series of steps or units are not limited to those explicitly listed but may include other steps or units that are not explicitly mentioned or are inherent to these processes, methods, systems, products, or equipment.

It is important to note that references to "first," "second," etc. in the disclosure are purely descriptive and do not imply relative importance or indicate the number of technical features. Thus, a feature identified as "first" or "second" may explicitly or implicitly include one or more such features. Additionally, technical solutions from different embodiments may be combined, but only if they can be implemented by those skilled in the field. If the combination of technical solutions is contradictory or impossible to realize, it shall be considered non-existent and outside the scope of protection provided by the disclosure.

It has been discovered for the first time that the levels of 17 metabolites, including taurine, homocysteine, uric acid, ascorbic acid, suberylglycine, uridine, dopamine 4-sulfate, inosinic acid, glyceraldehyde phosphate, [3-methoxy-4-(phosphoryl)phenyl] carbonyl sulfonic acid, nuclomedone, n4-cyclopropyl-6-(2,3-dichlorophenyl)-1,2,3,4-tetrahydropyrimidine-2,4-diimine, 1-[2-chlorine-2-(2,4-dichlorophenyl)ethenyl]-1,2,4-triazole, tetrachlorophthalic anhydride, malotilate, fulvic acid, and L-neopterin, are associated with drug-resistant tuberculosis (TB). Metabonomics analysis reveals a significant difference in the levels of these 17 metabolites between patients with drug-resistant tuberculosis and those with sensitive tuberculosis. As a result, a serum metabolic biomarker panel for detecting drug-resistant tuberculosis is provided.

In this embodiment, the serum metabolic biomarker panel for detecting drug-resistant tuberculosis comprises the aforementioned 17 serum metabolites present in patients with tuberculosis, namely, aurine, homocysteine, uric acid, ascorbic acid, suberylglycine, uridine, dopamine 4-sulfate, inosinic acid, glyceraldehyde phosphate, [3-methoxy-4-(phosphoryl)phenyl] carbonyl sulfonic acid, nuclomedone, n4-cyclopropyl-6-(2,3-dichlorophenyl)-1,2,3,4-tetrahydropyrimidine-2,4-diimine, 1-[2-chlorine-2-(2,4-dichlorophenyl)ethenyl]-1,2,4-triazole, tetrachlorophthalic anhydride, malotilate, fulvic acid, and L-neopterin. To elucidate the method for screening these 17 metabolites, the following description will be provided.

In this embodiment, a kit is provided which includes serum metabolic biomarkers for detecting drug-resistant tuberculosis. These biomarkers consist of the 17 metabolites present in the serum of patients with tuberculosis, as described above. The method for detecting drug-resistant tuberculosis will be explained in the following section. The screening method comprises the following steps:

In Step 1, the study enrolls the research subjects.

A total of 228 participants were recruited from Hangzhou Red Cross Hospital and the Second Affiliated Hospital of Zhejiang University between 2020 and 2021. The sample involves 110 individuals with drug-resistant tuberculosis (TB) and 118 healthy individuals. The diagnosis of drug-resistant tuberculosis was based on the following criteria: (A) positive trans-bacterial culture, (B) positive sputum smear, (C) positive MTB cultures, (D) positive nucleic acid detection for MTB, (E) chest radiograph (X-ray or CT scan), and (F) pulmonary histopathology diagnosis of TB.

In Step 2, the blood samples undergo pre-treatment.

1-2 mL of venous blood (to prevent lipolysis and hemolysis) is collected and injected into a vacuum blood collection tube. The tube is immediately inverted 5-8 times to ensure thorough mixing of the coagulant adhering to the tube wall with the blood. Subsequently, the tube is kept at room temperature (20° C.-25° C.) for approximately 30 minutes to allow complete clotting of the blood. Once the serum has fully separated, it is centrifuged at 3500 rpm for 10 minutes. Careful aspiration of approximately 0.3-1.5 mL of the clear liquid from the top layer is performed, and the obtained serum is transferred into a tightly sealed centrifuge tube. The tube's seal is checked, and the centrifuge tube is placed in a sample box and stored at −80° C.

In Step 3, machine detection is performed.

The iron particle-assisted laser desorption/ionization mass spectrometry (LDI-MS) technique is employed, utilizing iron particles dispersed in water at a concentration of 1 mg/mL as the matrix. The diluted serum (1 μL) is directly spotted onto a polished plate, air-dried at room temperature, and subsequently mixed with 1 μL of the matrix solution prior to LDI-MS analysis. Mass spectra are acquired using an AutoFlex TOF/TOF mass spectrometer (Bruker, Germany) equipped with a Nd:YAG laser (2 kHz, 355 nm). The acquisition is conducted in a positive reflection ion mode with delayed extraction. The repetition frequency is set at 1000 Hz, and the acceleration voltage is maintained at 20 kV. The delay time is optimized at 250 ns for all LDI-MS experiments. Each analysis involves 2000 laser shots. Following the acquisition of the raw mass spectrometry data (as depicted in FIG. 1), MATLAB code (R2016a, The MathWorks, USA) is employed for peak picking, alignment, normalization, and standardization preprocessing, thus transforming the raw data into a suitable format for subsequent analysis.

In Step 4, disease models are constructed based on machine learning.

A detection model is established utilizing the partial least squares (PLS) algorithm. For learning purposes, ¾ of the tuberculosis and healthy serum sample data are randomly selected as the training set, while the remaining ¼ is allocated as the test set. By employing this training set, the disease model is developed. Subsequently, a receiver operating characteristic (ROC) curve is plotted, and the area under the curve (AUC) of the model is calculated to be 83.9%.

In Step 5, metabolites are screened.

Differential metabolites are identified based on specific criteria. Metabolites with a VIP value greater than 1, model selection frequency exceeding 90%, and a p-value lower than 0.05 are selected as the differential metabolites. These include 17 metabolites, as presented in Table 1.

In Step 6, a drug-resistant tuberculosis detection model is established utilizing the partial least squares (PLS) algorithm. The model is developed based on the 17 identified differential metabolites, and a receiver operating characteristic (ROC) curve is plotted to evaluate its performance.

Figure 2:
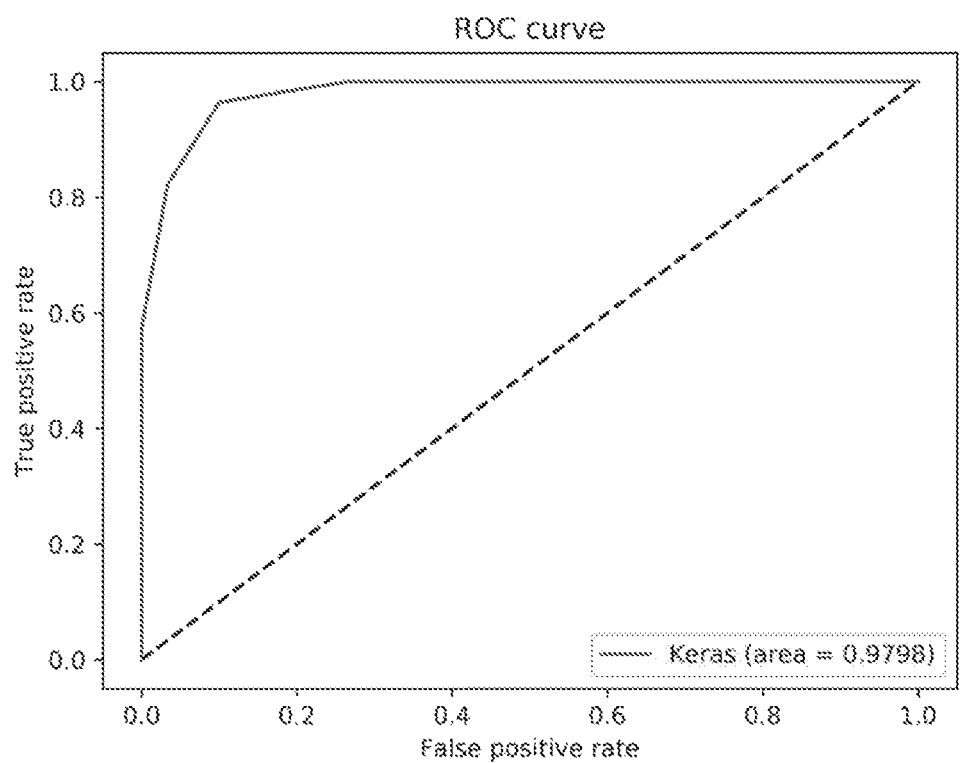
FIG. 2 illustrates a classification performance of a drug-resistant tuberculosis detection constructed using 17 serum metabolic biomarkers.

The classification performance of the drug-resistant tuberculosis detection model is illustrated in FIG. 2, demonstrating an area under the curve (AUC) of 98%, sensitivity of 90%, and specificity of 96%. In conclusion, the accuracy and specificity of drug-resistant tuberculosis detection utilizing the 17 serum metabolic markers are deemed satisfactory. The tuberculosis detection process involves the utilization of the drug-resistant tuberculosis detection model, encompassing the following steps.

The blood samples are processed following the methodology described in Step 2 above. Subsequently, raw metabolic fingerprints are acquired using the procedure outlined in Step 3. The data obtained from the previous step is then input into the model established using the 17 serum metabolic markers in Step 6. By analyzing the model output, it becomes feasible to determine whether an individual's blood sample tests positive for drug-resistant tuberculosis. The drug-resistant tuberculosis detection is conducted using the drug-resistant tuberculosis detection kit, employing the subsequent steps.

The blood sample undergoes pretreatment as described in Step 2. Subsequently, the tuberculosis detection kit is utilized to assess the levels of the 17 serum metabolic biomarkers mentioned earlier. The analysis of these biomarkers' levels aids in determining the presence of tuberculosis.

TABLE 1

A list of differential metabolites

| Number | Name of potential substance | m/z | HMDB ID |
|---|---|---|---|
| 1 | taurine | 164.102 | HMDB0000251 |
| 2 | homocysteine | 174.048 | HMDB0000742 |
| 3 | uric acid | 207.077 | HMDB0000289 |
| 4 | ascorbic acid | 214.952 | HMDB0000044 |
| 5 | glyceraldehyde phosphate | 220.893 | HMDB0252837 |
| 6 | suberylglycine | 254.012 | HMDB0000953 |
| 7 | uridine | 266.973 | HMDB0000296 |
| 8 | dopamine 4-sulfate | 271.967 | HMDB0004148 |
| 9 | L-neopterin | 292.082 | HMDB0000727 |
| 10 | [3-methoxy-4-(phosphoryl)phenyl] carbonyl sulfonic acid | 294.962 | HMDB0258589 |
| 11 | nuclomedone | 294.962 | HMDB02SS816 |
| 12 | n4-cyclopropyl-6-(2,3-dichlorophenyl)-1,2,3,4-tetrahydropyrimidine-2,4-diimine | 294.962 | HMDB0258956 |
| 13 | 1-[2-chlorine-2-(2,4-dichlorophenyl)ethenyl]-1,2,4-triazole | 295.908 | HMDB0254162 |
| 14 | tetrachlorophthalic anhydride | 322.728 | HMDB0258873 |
| 15 | malotilate | 326.913 | HMDB0254316 |
| 16 | fulvic acid | 330.962 | HMDB0252514 |
| 17 | inosinic acid | 348.962 | HMDB0000175 |

It is important to note that the numbering of the embodiments in this disclosure is purely for descriptive purposes and does not imply any advantages or disadvantages of the embodiments. Furthermore, in this disclosure, the term "including," "include," or any other variants is intended to encompass a non-exclusive range. Therefore, when referring to processes, devices, items, or methods, the inclusion of a series of elements not only encompasses the listed elements but also includes other unlisted elements or inherent elements of such processes, devices, items, or methods. The use of the phrase "including a . . . " does not preclude the existence of other similar elements in the aforementioned processes, devices, items, or methods.

The preferred embodiments of the invention disclosed above are provided solely to assist in understanding the invention and its details. These embodiments do not encompass all aspects and do not limit the invention to a specific embodiment. Clearly, based on the contents of this instruction manual, numerous modifications and variations can be made. The embodiments selected and described in detail in this specification are chosen to better explain the principles and practical applications of the invention, thereby enabling technical personnel in the relevant field to better comprehend and utilize the invention. The scope of the invention is defined only by the claims and their complete scope and equivalents.

The aforementioned embodiments represent preferred examples of this disclosure, but they do not limit the scope of the patent for this disclosure. Any equivalent structures or processes derived from the description and drawings of this disclosure, whether applied directly or indirectly in other related technical fields, should be similarly encompassed within the scope of patent protection for this disclosure.

The invention claimed is:

1. A composition serving as a biomarker panel for detecting drug-resistant tuberculosis, comprising detecting reagents, and 17 serum metabolites, wherein the detecting reagents comprise an iron particle matrix, and the 17 serum metabolites consist of taurine, homocysteine, uric acid, ascorbic acid, suberylglycine, uridine, dopamine 4-sulfate, inosinic acid, glyceraldehyde phosphate, [3-methoxy-4-(phosphoryl)phenyl]carbonyl sulfonic acid, nuclomedone, n4-cyclopropyl-6-(2,3-dichlorophenyl)-1,2,3,4-tetrahydro-pyrimidine-2,4-diimine, 1-[2-chlorine-2-(2,4-dichlorophenyl)ethenyl]-1,2,4-triazole, tetrachlorophthalic anhydride, malotilate, fulvic acid, and L-neopterin, the biomarker panel is utilized for differential diagnosis of drug-resistant tuberculosis.

* * * * *